United States Patent [19]

Kronman

[11] Patent Number: 4,969,906
[45] Date of Patent: Nov. 13, 1990

[54] BONE AND BONY TISSUE REPLACEMENT

[76] Inventor: Joseph H. Kronman, 27 Oakland Ave., Needham, Mass. 02192

[21] Appl. No.: 323,037

[22] Filed: Mar. 10, 1989

Related U.S. Application Data

[63] Continuation of Ser. No. 78,535, Jul. 28, 1987, abandoned.

[51] Int. Cl.$^5$ .............................................. A61F 2/28
[52] U.S. Cl. ...................................... 623/16; 623/11; 623/66; 433/201.1; 424/81; 606/76
[58] Field of Search ....... 128/92 YW, 92 YQ, 92 YR, 128/92 YG; 264/26; 424/81; 433/201.1, 212, 223; 623/11, 66, 16; 106/35; 606/76

[56] References Cited

U.S. PATENT DOCUMENTS

| | | |
|---|---|---|
| 3,618,213 | 11/1971 | Shepherd et al. ........................ 32/2 |
| 3,628,248 | 12/1971 | Kroder et al. .......................... 32/10 |
| 3,784,540 | 1/1974 | Kliment et al. ..................... 260/86.1 |
| 4,141,864 | 2/1979 | Rijke et al. ........................... 433/173 |
| 4,199,864 | 4/1980 | Ashman ............................... 433/175 |
| 4,452,776 | 6/1984 | Refojo ..................................... 424/81 |
| 4,535,485 | 8/1985 | Ashman et al. ....................... 623/16 |
| 4,536,158 | 8/1985 | Bruins et al. ...................... 433/201.1 |
| 4,725,273 | 2/1988 | Kira ........................................ 623/66 |
| 4,728,570 | 3/1988 | Ashman et al. ....................... 623/16 |

OTHER PUBLICATIONS

CRC Handbook of Chemistry and Physics, Weast (editor), 64th Ed., (1983), p. F-114.
"Effect of the Structure of Poly(Glycol Monomethacrylate) Gel on the Calcification of Implants", L. Sprincl et al., Calc. Tiss. Res. 13, 63–72 (1973).
"Biological Tolerance of Ionogenic Hydrophilic Gels", L. Sprincl et al., J. Biomed. Mater. Res. 7, 123–136 (1973).
"Poly—HEMA Sponge: A Biocompatible Calcification Implant", J. H. Kronman et al., Biomat., Med. Dev., Art. Org., 7(2), 299–305 (1979).
"Prevention of Alveolar Bone Loss Postextraction with HTR Grafting Material", A. Ashman et al., Oral Surgery, Oral Medicine, Oral Pathology, 60(2), 146–153 (1985).
Summary and description Hard Tissue Replacement (HTR) Medical Biological Sciences, Inc.
"HTR (Hard Tissue Replacement) for Edentulous Ridge Augmentation", A. Ashman et al., material from Medical Biological Sciences, Inc.).

Primary Examiner—Randall L. Green
Assistant Examiner—Paul Prebilic
Attorney, Agent, or Firm—Lahive & Cockfield

[57] ABSTRACT

A new type of implant for replacement of bone or bony tissue has been developed. The implant is formed of a hydrophilic polymer having a random distribution of single size pores throughout. This hydrophilic polymer is implanted in an uncalcified, or partially calcified, state and is allowed to calcify in place, throughout its entire body, through the random pores. The hydrophilic material can be made from materials such as hydrophilic acrylates and hydrophilic methacrylates.

23 Claims, 1 Drawing Sheet

PRIOR ART

BONE AND BONY TISSUE REPLACEMENT

REFERENCE TO RELATED APPLICATIONS

This application is a continuation of application Ser. No. 078,535, filed July 28, 1987, now abandoned.

BACKGROUND OF THE INVENTION

The present invention relates to implantable materials for replacement of bone or bony tissue. More particularly, the present invention relates to a method of making hydrophilic polymeric implants having controlled pore size which can be shaped and used to replace bone or bony calcified tissue in animals and man.

For many years people have been searching for materials useful as replacements for different types of tissue. Materials tried include silicones, acrylates and other plastics, and metals. While each of these materials has certain advantages, some problems have developed in use. For example, silicone becomes hardened and displaced over time so its use as a breast augmentation implant, while tried often in the 1960's, has declined. Similarly, although metals and some plastic materials have been used for joints and other bone replacements, rejection problems have limited the use to those with no other alternatives. Plastics have also been tried as both soft and hard tissue replacements but there have been similar problems.

Because of these Problems with the materials tried to date, a great deal of attention has been focused on modified plastics, particularly the acrylates and methacrylates, for implantation. Because of their transparent nature and easy moldability, there has been special emphasis on the dental and optical uses of the acrylate family. The optical uses have included several buckles and lens replacements while the dental area has focused on tooth and alveolar ridge replacement. In addition, some work has been done on breast or soft tissue replacement using acrylates and methacrylates. The acrylates and methacrylates, when implanted in a porous form, show tissue ingrowth and/or calcification which may support or harden the implant; in many cases, this ingrowth or calcification has been a problem while in others it is necessary.

The Kroder et al. U.S. Pat. No. 3,628,248 is an example of the uses tried for the acrylates and methacrylates. This patent discloses a process for forming artificial implants, preferably for dental uses, using a variety of plastics, most preferably the acrylates and methacrylates. Kroder attempts to encourage tissue growth into the material using a porous surface. They obtain a porous surface by mixing potassium chloride in the acrylate monomer before polymerization. The potassium chloride is then leached out of the outer surface, leaving pores. However, the initiator used by Kroder as a hydrophobic could cause problems with tissue rejection. The use of hydrophobic plastics such as that shown by Kroder could also produce problems with rejection since there cannot be any transfer of electrolytes across the implant.

U.S. Pat. No. 4,199,864, issued on application by Ashman, attempted to cure the problems with the Kroder material. Ashman used polymethyl methacrylate as a dental implant material, and tried to form a porous surface by mixing a salt with the hydrophobic material. In fact, Ashman also lined the mold before polymerization with the salt crystals to provide surface porosity. Ashman found that even doing this, a "skin" formed over the plastic so it was necessary to grind off the outer layer of the material to expose the crystals. After exposure, Ashman let the material soak in water in an attempt to leach the salt crystals out. However, this just removed the salt from the outer layer because of the hydrophobicity of the material. Again, the hydrophobic material itself could still cause rejection problems.

In U.S. Pat. No. 4,536,158, issued to Bruins and Ashman and assigned to the same assignee as the Ashman patent, the same polymethyl methacrylate material was used for a dental implant. In this patent, the hydrophobic material was coated with a small amount of a hydrophilic methacrylate, hydroxyethyl methacrylate (HEMA) in an attempt to reduce rejection. The Bruins et al. patent describes using the material for replacing bone for dental applications. Very small particles of the coated hydrophobic material is made into a porous filler by packing the particles so that pseudopores are formed between the individual particles. While this approach is fine for a nonweight-bearing application, its overall usefulness is limited. This material is sold commercially by Medical Biological Sciences, Inc., under the trade name HTR.

Others have used acrylates in various ways in order to replace bone or fibrous tissue. For example, U.S. Pat. No. 3,609,867 and U.S. Pat. No. 3,789,029, both issued to Hodash, concern an acrylate/ground bone mixture while U.S. Pat. No. 3,713,860, issued to Aushern, discloses a mixture of a porous aluminum oxide and a methyl methacrylate polymer to form a bone replacement substitute.

None of these bone or fibrous tissue substitutes have solved all the problems with rejection and controlled ingrowth. Accordingly, HEMA has been one of the newer materials tried for a variety of implantation and surgical uses. For example, in U.S. Pat. No. 4,452,776, issued on an application of Refojo, HEMA is used not only as a replacement for acrylates for contact lenses but also as a scieral buckle. HEMA has also been used as a breast augmentation material and as a dental implant. See Kronman et al., "Poly-HEMA Sponge: A Biocompatible Calcification Implant", Biomat., Med. Dev., Art. Org., 7(2):299-305 (1979). HEMA has been used as an implant material in both a porous and nonporous state. However, the only method of obtaining porous HEMA has been to polymerize the hydroxyethyl methacrylate monomer about water molecules. For examPle, the Kronman et al. article discusses both 70/30 and 80/20% HEMA/water mixtures. Polymerizing about water molecules forms micropores within the hydrophilic HEMA but it does not allow any way to control the pore size with accuracy. Further, there is no way of being sure that the pores range throughout the material.

Problems with uncontrolled pore size besides the question of whether the pores are evenly distributed throughout the material include the problem that the properties of HEMA after implantation are different depending upon pore size. For example, with a pore size of 60-150 $\mu$, calcification takes place, leading to a bone-like implant. If the pore size is between 225 to 275 $\mu$, the properties of the material after implantation are similar to those of cartilage while a pore size of 300 to 450 $\mu$ yields a fibrous-like tissue, similar to fibrous connective tissues.

Accordingly, an object of the invention is to provide a method making a material for forming a synthetic bone-like implant of a biocompatible material which does not cause rejection and promotes ingrowth and calcification.

Another object of the invention is to provide a method of forming a biocompatible bony tissue replacement.

A further object of the invention is to provide a biocompatible and shapable bone-like implant material with a variety of uses, e.g., dental bone and tooth replacement, cosmetic surgery and long bone replacement.

A still further object of the invention is to provide a biocompatible synthetic replacement for bone or bony tissue which could be used for bone augmentation, e.g., hard palate augmentation.

These and other objects and features of the invention will be apparent from the following description and the drawings.

SUMMARY OF THE INVENTION

The invention disclosed herein provides a method of making a biocompatible microporous implant having controlled pore size for replacement of bone or bony calcified tissue in an animal, particularly man. The invention also features the implant itself as well as its uses, e.g., dental uses, cosmetic surgery or reshaping, and long bone replacement or augmentation.

The microporous implantable material of the invention is formed by dispersing crystals of a water-dissolvable material, preferably a crystalline salt such as sodium chloride, potassium chloride or calcium chloride, in an unpolymerized hydrophilic polymerizable monomer. To make synthetic bony tissue-like material, crystals of the water-dissolvable material ranging from about 50 to 200 $\mu$, preferably 60 to 150 $\mu$ in diameter, are mixed with the monomer. The hydrophilic polymerizable monomer is polymerized about the crystals to form a hydrophilic polymeric material having crystals dispersed therethrough. The resulting material is contacted with a sufficient amount of an aqueous solution to dissolve the crystals, thereby forming a polymerized microporous material having micropores of about 50 to 200 $\mu$ in diameter at the locations where the crystals had previously been. This microporous material may then be implanted in animals or human hosts at nonweight-bearing locations such as the axillary fold to partially calcify. After partial calcification, the material is then formed into the implant of the invention. For some uses, the implant may be made in several pieces and combined into a single piece.

The monomers may be any hydrophilic acrylates or methacrylates but are preferably hydroxyalkyl acrylates or methacrylates, most preferably hydroxyethyl methacrylate. The hydrophilic polymeric material may consist of a mixture of the hydrophilic materials but a homopolymer of hydroxyethyl methacrylate is preferred. The polymerization reaction is carried out using standard methods, e.g., using an initiator, heat polymerization, or UV radiation.

The ratio by weight of the hydrophilic polymeric material after polymerization to the crystal can be controlled to produce the properties desired, e.g., changes in weight ratio can lead to different degrees of calcification and ingrowth. In addition, the ratio of salt volume to polymer volume can be used to determine some properties of the resulting material.

The invention also features an implant for replacement of bone or bony tissue made by the method of the invention. If the implant is made having micropores ranging from about 50 to about 200 $\mu$ it calcifies to form a bone-like material. This material is particularly well adapted for a dental implants and the same type of bony replacement material may be used for cosmetic surgery or long bone replacement. The dental implants for the invention are useful for replacement of teeth, alveolar bone, or hard palate reshaping while the cosmetic surgery uses include bone reshaping and replacement. The long bone implants can be used to replace arm or leg bones or to augment bones which have deteriorated due to a variety of conditions such as osteoporosis or other degenerative bone diseases. In addition, the material can be used to form partial or complete digit replacements.

DESCRIPTION

As noted, the present invention features a method of producing biocompatible implants for replacement of bone and calcified bony tissue. The implants of the invention promote tissue ingrowth while undergoing bone-like hardening due to calcification. The invention provides a method of Producing micropores of controlled size dispersed throughout a hydrophilic material, yielding an implant which is biocompatible and has pores necessary for calcification and tissue ingrowth throughout the implant. Controlling the pore size permits control of the properties of the final material since changes in the amount of calcification or tissue ingrowth changes the texture of the initially sponge-like replacement material. In this manner, synthetic bone or bony calcified tissue is produced under controlled conditions. This method prevents the uncontrolled, uneven calcification or other hardening which occurs in many other types of implants and thereby limits their usefulness.

Figure 1:
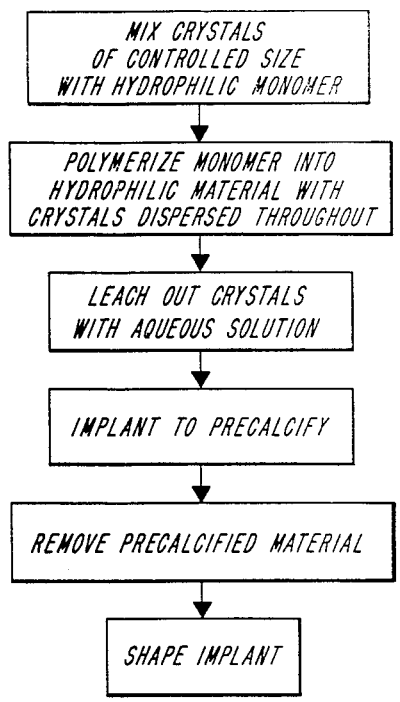
FIG. 1 is a flow chart showing the steps in the manufacturing process for the implant of the present invention.

FIG. 1 is a schematic diagram of the method of the invention. Crystals of a water-dissolvable material, preferably a salt such as sodium chloride, are milled into a controlled size selected depending on the type of tissue desired to be replaced. The pore size of the salt crystals should be about 50 to 200 $\mu$ in diameter. Salt crystals of that size would be selected so that upon solubilization, they would leave the desired pores. The salt crystals are mixed with an unpolymerized monomer of the implant material, e.g., hydroxyethyl acrylate.

One method exemplary of the invention has sodium chloride crystals milled to a size of about 125 $\mu$ dispersed throughout a solution of unpolymerized hydroxyethyl methacrylate. Approximately 67.8g of sodium chloride is dispersed in 150ml of the hydroxyethyl methacrylate monomer in a 200ml beaker, yielding a final volume ratio of 75% Plastic, 25% salt after polymerization. One method of keeping the salt crystals in a solution is by a magnetic stirrer which disperses the crystals in an even manner throughout the solution while it is undergoing polymerization. Alternatively, the materials are mixed and placed in a beaker or ampule. In either case, the solution is bubbled with nitrogen for thirty minutes, then sealed and polymerized. Polymerization is carried out in a conventional manner, e.g., using an initiator such as benzoyl peroxide but for some uses heat or UV polymerization is preferred since there cannot be any initiator remaining after polymerization which can cause rejection effects in the body.

A preferred polymerization technique has the sealed solution polymerized with an initiator in a thermostat at 60° C. for approximately ten hours. Approximately $5-10\times10^{-3}$ mole of the initiator, preferably methyl azo-bis isobutyrate is used per 1,000g of monomer. See "Effect of the Structure of Poly(Glycol Monomethacrylate) Gel on the Calcification of Implants", Sprincl, Kopecek and Lim, Calc. Tiss. Res. 13:63–72 (1973), for exemplary procedures of polymerization.

The procedures described will yield a block of the polymer with the salt crystals dispersed therein. Accordingly, it is necessary to remove the salt crystals in order to form the micropores. Since the polyhydroxyethyl methacrylate is hydrophilic, contacting the material with an aqueous solution leaches the salt crystals. The hydrophilic characteristics of the material allows the aqueous solution to permeate the material and dissolves the salt crystals from the entire body of the implant, as well as allowing the dissolved salt to flow freely from the material. Leaching of the salt crystals can be carried out by placing the material in a large excess of water or another aqueous based solution, preferably at an elevated temperature. It is also possible to use a flow system which constantly replenishes the aqueous solution, keeping the salinity of the surrounding water down and yielding better salt dissolution kinetics.

In one exemplary procedure, the block of polymerized material is placed in a 200 ml beaker under running water for about one hour. The block is removed, rinsed and allowed to stand in fresh water for about ten minutes. A pH meter with an ion probe is used to test for ion concentration, indicating whether salt is still leaching. If no salt is detected, the material can be shaped but if ions are detected, further soaking is used to leach the remaining salt.

Leaching the salt crystals from the polymerized material leaves a microporous material having pores where the salt crystals were previously. The salt is dissolved throughout the entire material because of the hydrophilicity of the material so the resulting material has pores throughout.

Figure 2:
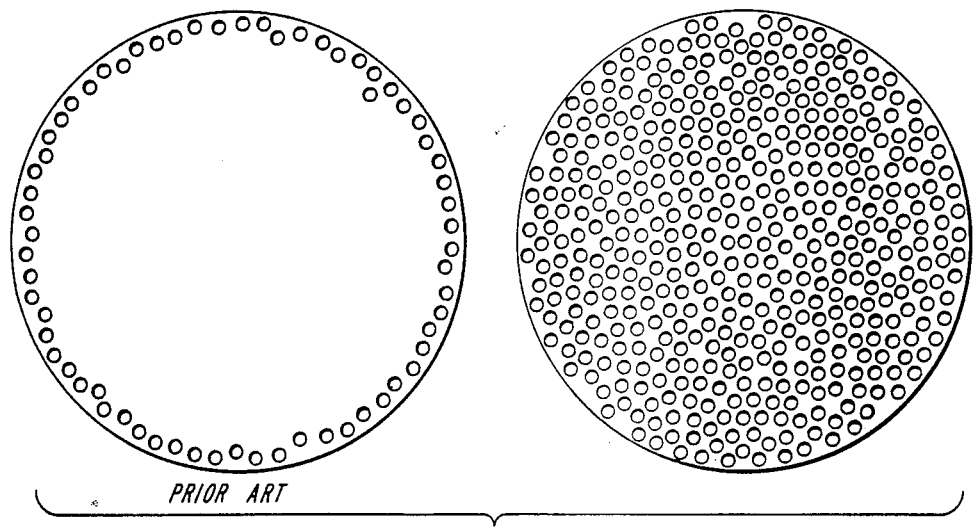
FIG. 2 shows a cross-section comparison of the material of the present invention with the prior art Ashman material.

In a hydrophobic material, such as that used by Ashman, the water cannot permeate past the outer layers of material and therefore salt crystals are entrapped within the body of the hydrophobic implant material. The entrapped salt cannot be contacted by the liquid and cannot dissolve. Accordingly, a cross-section of the Ashman-type material will have pores only on the outer layer. The portion of FIG. 2 labeled Prior Art illustrates the Ashman material. In fact, since a film or outer coating may form over the material during polymerization, it may be necessary to grind the outer surfaces of the material in order to obtain access to any of the salt crystals if a hydrophobic material is used. This type of grinding, specifically described in Ashman, is necessitated by his choice of materials.

In contrast, the material of the present invention will have pores throughout. The portion of FIG. 2 marked Present Invention shows the extent of the pores using the method described herein.

Once one obtains the microporous material, precalcification may be used, particularly if the implant is going to be weight-bearing. The microporous material is precalcified by implantation into the host at a non-weight-bearing location, e.g., the axillary fold. The implant is allowed to remain for several weeks until partial calcification occurs, and is then removed and shaped in a conventional manner, e.g., cutting or grinding. An advantage of the material of the invention is that once formed, the gel is sponge-like so shaping can be carried out by carving with a scalpel or scissors. The Refojo U.S. Pat. No. 4,452,776, has a description of other ways of forming poly-HEMA into a proper shape. For certain uses, it may be possible to form a mold to the proper shape and polymerize the material directly in that mold. Such preshaping is included within the present invention. The implant may be multipiece or a single piece depending on size and strength requirements.

The implantation techniques using the material of the invention include those currently known and are not in and of themselves part of the present invention. Common cosmetic surgery techniques for replacement or augmentation of tissue have been described in the literature and need not be described further herein. However, the material of the present invention is biocompatible and has pores which allow for ingrowth of fibrous tissue which allow implantation without the problems caused by tissue rejection. In part, rejection is minimized because the hydrophilic nature of the material used herein allows free flow of electrolytes and liquids across the implant. In fact, HEMA has been used as a coating on a number of metal or plastic implants in order to minimize rejection.

The uses set forth herein are exemplary only and others skilled in the art will determine other uses and modifications of the method and implant disclosed herein. Such other modifications and uses are within the scope of the following claims.

What is claimed is:

1. A microporous implant having controlled pore size for replacement of bone or bony calcified tissue comprising a hydrophilic polymeric material having pores, formed before implantation of said implant, of a single controlled pore size randomly distributed throughout substantially all of the body of said implant, said pores comprising a single pore size in a selected range of about 50 to about 200$\mu$ in diameter, said pores being formed in said polymeric material by:
   (a) dispersing water-dissolvable salt crystals of a size corresponding to said single pore size in an unpolymerized monomer of a hydrophilic polymerizable material;
   (b) polymerizing said monomer with said salt crystals dispersed therein to form a polymeric material with salt crystals randomly dispersed throughout substantially all of said implant;
   (c) subjecting said polymeric material with salt crystals dispersed therein to an aqueous solution in vitro whereby said salt crystals are dissolved, and form said pores in said polymeric material at locations previously occupied by said salt crystals; and
   (d) shaping said polymeric material into said implant.

2. The implant of claim 1 wherein said monomer is selected from a group consisting of monomers of hydrophilic acrylates and hydrophilic methacrylates.

3. The implant of claim 2 wherein said hydrophilic acrylates comprise hydroxyalkyl acrylates.

4. The implant claim 2 wherein said hydrophilic methacrylates comprise hydroxyalkyl methacrylates.

5. The implant of claim 4 wherein said hydroxyalkyl methacrylates comprise hydroxyethyl methacrylate.

6. The implant of claim 5 wherein said hydrophilic polymeric material consists essentially of a homopolymer of hydroxyethyl methacrylate.

7. The implant of claim 1 wherein said salt crystals are selected from a group consisting of sodium chloride, potassium chloride and calcium chloride.

8. The implant of claim 1 wherein said hydrophilic polymeric material comprises polyhydroxyethyl methacrylate and said salt crystals comprise sodium chloride.

9. A synthetic bony tissue implant adapted for dental implantation comprising a shaped, partially calcified microporous hydrophilic polymeric material having pores, formed before implantation, of a single controlled pore size randomly distributed throughout substantially all of the body of said implant, said pores comprising a single pore size selected from a range of about 50 to about 200 $\mu$ in diameter, said hydrophilic polymeric material selected from a group consisting of hydrophilic acrylates, hydrophilic methacrylates, and mixtures thereof.

10. The implant of claim 9 wherein said micropores are formed by the method of mixing at least one monomer of said hydrophilic polymeric material with crystals of a water-dissolvable salt, said salt crystals ranging in size from about 50 to about 200 $\mu$ in diameter, polymerizing said monomer to form said hydrophilic polymeric material, and dissolving said salt crystals by contacting the resulting hydrophilic polymeric material with an aqueous solution to produce said micropores.

11. The implant of claim 10 wherein said salt crystals are selected from a group consisting of sodium chloride, potassium chloride and calcium chloride.

12. The implant of claim 10 wherein the material forming said implant material is partially calcified by implantation in an animal or human host before it is shaped.

13. The implant of claim 9 wherein said implant is used for replacement of alveolar bone.

14. The implant of claim 9 wherein said implant is used for replacement of tooth surfaces.

15. The implant of claim 9 wherein said implant is used for mandibular replacement.

16. The implant of claim 9 wherein said implant is used for hard palate augmentation.

17. The implant of claim 9 wherein said hydrophilic acrylates comprises hydroxyalkyl acrylates.

18. The implant of claim 9 wherein said hydrophilic methacrylates comprise hydroxyalkyl methacrylates.

19. The implant of claim 18 wherein said hydroxyalkyl methacrylates comprise hydroxyethyl methacrylate.

20. The implant of claim 1 wherein said implant comprises a synthetic bony tissue implant adapted for cosmetic surgery.

21. The implant of claim 1 wherein said implant comprises a strong bone implant adapted for replacing or augmenting leg or arm bones.

22. The implant of claim 1 wherein said implant comprises a digit implant adapted for replacing or augmenting digits.

23. The implant of claim 1 wherein said implant comprises a joint implant adapted for replacing or augmenting joints.

* * * * *